(12) United States Patent
Bianchessi et al.

(10) Patent No.: US 10,190,161 B2
(45) Date of Patent: *Jan. 29, 2019

(54) APPARATUS AND METHOD FOR NUCLEIC ACID SEQUENCING BASED ON NANOWIRE DETECTORS

(71) Applicant: STMICROELECTRONICS S.R.L., Agrate Brianza (IT)

(72) Inventors: Marco Angelo Bianchessi, Melzo (IT); Francesco Ferrara, Monteroni di Lecce (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 364 days.

This patent is subject to a terminal disclaimer.

(21) Appl. No.: 14/676,618

(22) Filed: Apr. 1, 2015

(65) Prior Publication Data

US 2015/0284792 A1 Oct. 8, 2015

(30) Foreign Application Priority Data

Apr. 3, 2014 (IT) .............. TO2014A0280

(51) Int. Cl.
*C12Q 1/68* (2018.01)
*C12P 19/34* (2006.01)
(Continued)

(52) U.S. Cl.
CPC ....... *C12Q 1/6874* (2013.01); *G01N 27/4146* (2013.01); *B82Y 30/00* (2013.01)

(58) Field of Classification Search
None
See application file for complete search history.

(56) References Cited

U.S. PATENT DOCUMENTS 8,262,879 B2 9/2012 Oliver
8,607,632 B2 12/2013 Meisel et al.
(Continued)

FOREIGN PATENT DOCUMENTS

CN 103275867 A 9/2013
EP 1 441 213 A1 7/2004
(Continued)

OTHER PUBLICATIONS

"DNA: An introduction to nanopore sequencing," Nanopore™ Techologies, retrieved from https://nanoporetech.com/technology/analytes-and-applications-dna-rna-proteins/dna-an-introduction-to-nanopore-sequencing, on Sep. 4, 2014, 2 pages.
(Continued)

*Primary Examiner* — Young J Kim
(74) *Attorney, Agent, or Firm* — Seed IP Law Group LLP

(57) ABSTRACT

An apparatus for nucleic acid sequencing includes: a base-detection device in a detection site, the base-detection device being configured to detect bases of a portion of a nucleic acid strand at the detection site; and a conveying device, configured to extend the nucleic acid strand and to cause the extended nucleic acid strand to slide through the detection site along a path. The base-detection device includes a plurality of field-effect nanowire detectors, arranged along the path and each including a respective nanowire and nucleic acid probes, which are defined by respective base sequences and are fixed to the respective nanowire.

22 Claims, 4 Drawing Sheets

(51) Int. Cl.
*C12Q 1/6874* (2018.01)
*G01N 27/414* (2006.01)
*B82Y 30/00* (2011.01)

(56) References Cited

U.S. PATENT DOCUMENTS

| | | | |
|---|---|---|---|
| 8,673,627 B2 | 3/2014 | Nobile et al. | |
| 8,882,980 B2 | 11/2014 | Ling et al. | |
| 9,765,326 B2* | 9/2017 | Ferrara | C12N 15/101 |
| 2003/0215816 A1 | 11/2003 | Sundararajan et al. | |
| 2006/0246497 A1* | 11/2006 | Huang | G01N 27/4146 435/6.14 |
| 2006/0275911 A1 | 12/2006 | Wang et al. | |
| 2007/0190543 A1 | 8/2007 | Livak | |
| 2008/0187915 A1 | 8/2008 | Polonsky et al. | |
| 2010/0327874 A1 | 12/2010 | Liu et al. | |
| 2011/0236984 A1* | 9/2011 | Sun | C12Q 1/6869 436/94 |
| 2012/0074925 A1 | 3/2012 | Oliver | |
| 2012/0264617 A1 | 10/2012 | Pettit | |
| 2013/0213815 A1 | 8/2013 | Tung et al. | |
| 2013/0260472 A1 | 10/2013 | Holt | |
| 2014/0193820 A1 | 7/2014 | Sun et al. | |
| 2015/0218630 A1 | 8/2015 | Sun et al. | |
| 2016/0274056 A1 | 9/2016 | Rothberg et al. | |

FOREIGN PATENT DOCUMENTS

| | | |
|---|---|---|
| EP | 1 645 628 A1 | 4/2006 |
| EP | 2 311 975 A1 | 4/2011 |
| WO | 02/31183 A1 | 4/2002 |
| WO | 2010/026488 A2 | 3/2010 |
| WO | 2013/012881 A2 | 1/2013 |
| WO | 2013/088098 A2 | 6/2013 |
| WO | 2014/059046 A1 | 4/2014 |

OTHER PUBLICATIONS

"Nanopore Group—About: Home," UC Santa Cruz, retrieved from http://nanopore.bme.ucsc.edu/about, on Sep. 4, 2014, 2 pages.
Branton et al., "The potential and challenges of nanopore sequencing," *Nature Biotechnology* 26(10):1146-1153, Oct. 2008.
Davies, "Oxford Strikes First in DNA Sequencing Nanopore Wars," Feb. 17, 2012, retrieved from http://www.bio-itworld.com/news/02/17/12/Oxford-strikes-first-in-DNA-sequencing-nanopore-wars.html, on Sep. 4, 2014, 3 pages.
Gao et al., "Silicon Nanowire Arrays for Label-Free Detection of DNA," *Anal. Chem.* 79(9):3291-3297, May 2007.
Gen, "Roche and IBM Set Sights on $100-1,000 Genome Nanopore Sequencing Platform," Jul. 1, 2010, retrieved from http://www.genengnews.com/gen-news-highlights/roche-and-ibm-set-sights-on-100-1-000-genome-nanopore-sequencing-platform/81243603/, on Sep. 4, 2014, 2 pages.
Iganacio-de Leon et al., "Size-selective molecular transport through silica colloidal nanopores," *Chem. Commun.* 47:553-555, 2011.
Karger et al., "Multiwavelength fluorescence detection for DNA sequencing using capillary electrophoresis," *Nucleic Acids Research* 19(18):4955-4962, 1991.
Kim et al., "An FET-type charge sensor for highly sensitive detection of DNA sequence," *Biosensors and Bioelectronics* 20:69-74, 2004.
Kumemura et al., "Single DNA Molecule Isolation and Trapping in a Microfluidic Device," *ChemPhysChem* 8:1875-1880, 2007.
LabGrab, "New DNA Sequencing Method Increases Speed While Decreasing Costs," Dec. 22, 2009, retrieved from http://www.labgrab.com/users/labgrab/blog/new-dna-sequencing-method-increases-speed-while-decreasing-costs, on Mar. 23, 2015, 2 pages.
Li et al., "Electrically moving single-stranded DNA into and out of double-walled carbon nanotubes," *Chem. Commun.* 47:2309-2311, 2011.
Liu et al., "Voltage-Driven Translocation of DNA through a High Throughput Conical Solid-State Nanopore," *PLOS ONE* 7(9) e46014:1-9, Sep. 2012.
Paulasova, P. et al., "The peptide nucleic acids (PNAs): a new generation of probes for genetic and cytogenetic analyses," Annales de Genetique, vol. 47, pp. 349-358, 2004.
Pollack, "Company Unveils DNA sequencing Device Meant to Be Portable, Disposable and Cheap," Feb. 17, 2012, The New York Times, retrieved from http://www.nytimes.com/2012/02/18/health/oxford-nanopore-unveils-tiny-dna-sequencing-device.html, on Sep. 4, 2014, 2 pages.
Pooga, M. et al., "PNA oligomers as tools for specific modulation of gene expression," Biomolecular Engineering, vol. 17, pp. 183-193, 2001.
Schaffer, "Nanopore Sequencing: Simple and direct analysis of DNA will make genetic testing routine in more situations.," May/Jun. 2012, MIT Technology Review, retrieved from http:www2.technologyreview.com/article/427677/nanopore-sequencing/, on Sep. 4, 2014, 2 pages.
Seong et al., "Single-Molecular AFM Probing of Specific DNA Sequencing Using RecA-Promoted Homologous Pairing and Strand Exchange,"*Anal. Chem.* 72(6):1288-1293, Mar. 2000.
Tsutsui et al., "Transverse electric field dragging of DNA in a nanochannel," *Scientific Reports* 2(394):1-7, May 2012.
Wanunu, "Nanopores: A journey towards DNA sequencing," *Physics of Life Reviews* 2(9):125-158, May 2012.
Zhang et al., "Highly sensitive measurements of PNA-DNA hybridization using oxide-etched silicon nanowire biosensors," *Biosensors and Bioelectronics* 23:1701-1707, 2008.

\* cited by examiner

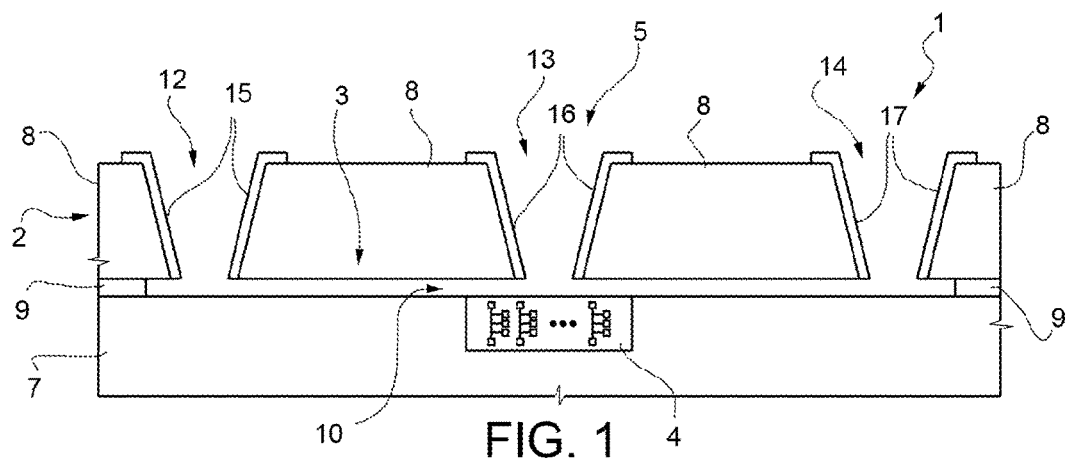

APPARATUS AND METHOD FOR NUCLEIC ACID SEQUENCING BASED ON NANOWIRE DETECTORS

BACKGROUND

Technical Field

The present disclosure relates to an apparatus and to a method for nucleic acid sequencing based upon nanowire detectors.

Description of the Related Art

Given the ever-increasing importance that nucleic acid sequencing is assuming, various techniques have been developed for determining the nucleotide sequence.

Some of the known techniques are based upon the division of a nucleic acid molecule into short fragments, in general of some hundreds of bases, which are sequenced individually. The information collected on the individual portions is subsequently processed and aggregated for reconstructing the entire sequence of the bases that form the nucleic acid molecule. Reconstruction of the sequence is, however, an operation that is extremely complex and consuming in terms of resources, in particular, processing capacity, and time. Furthermore, it may happen that some fragments are not read and reconstructed correctly, and thus sequencing may be incomplete.

The developments in the nanotechnology sector have enabled development of new devices and techniques that enable handling of individual molecules, exploiting, in particular, the electrical charge with which the nucleic acids are provided. For instance, in some devices appropriate electrical fields are used to cause passage of a single nucleic acid molecule through a nanopore in a membrane. In practice, the device has two chambers separated by a membrane, which has a nanopore and is provided with electrodes that enable creation of an electrical field. A solution containing molecules of a nucleic acid is loaded into one of the two chambers. Then, one end of a nucleic acid molecule, which normally presents as an entangled strand, may be introduced into the nanopore thanks to the electrical field. The dimensions of the nanopore are such that the presence of a portion of one molecule inhibits entry of ends of further molecules (the diameter of the nanopore may, for example, be between 5 nm and 10 nm). In this way, it is possible to isolate and handle a single sequence. The force exerted by the electrical field causes the strand forming the molecule to extend as it passes through the nanopore following after the end. The strand thus extended may be analyzed for sequencing.

Examples of devices of this type are described in Liu Q., Wu H., Wu L., Xie X., Kong J., et al. (2012), "Voltage-Driven Translocation of DNA through a High Throughput Conical Solid-State Nanopore", PLoS ONE 7(9): e46014; DOI:10.1371/journal.pone.0046014; and in Tsutsui, M. et al., "Transverse Electric Field Dragging of DNA in a Nanochannel" Sci. Rep. 2, 394; DOI:10.1038/srep00394 (2012).

The detection techniques available, however, still enable identification only of relatively short sequences of bases, up to some thousands in the most favorable cases. There thus remains the need to recompose the partial sequences, with associated computational burden and possibility of errors.

BRIEF SUMMARY

At least one embodiment of the present disclosure provides an apparatus and a method for nucleic acid sequencing that will enable the limitations described above to be overcome.

One embodiment of the present disclosure is an apparatus for nucleic acid sequencing. The apparatus includes a base-detection device in a detection site and a conveying device. The base-detection device is configured to detect bases of a portion of a nucleic acid strand at the detection site. The conveying device is configured to extend the nucleic acid strand and to cause the extended nucleic acid strand to slide through the detection site along a path. The base-detection device comprises a plurality of field-effect nanowire detectors arranged along the path and each including a respective nanowire and nucleic acid probes, which are defined by respective base sequences and are fixed to the respective nanowire.

BRIEF DESCRIPTION OF THE SEVERAL VIEWS OF THE DRAWINGS

For a better understanding of the disclosure, some embodiments thereof will now be described, purely by way of non-limiting example and with reference to the attached drawings, wherein:

FIG. 1 is a cross-section through a body integrating a portion of an apparatus for nucleic acid sequencing according to an embodiment of the present disclosure;

FIG. 2 is a top plan view of the body of FIG. 1;

FIG. 3 is a block diagram of the apparatus of FIG. 1;

DETAILED DESCRIPTION

Figure 4:
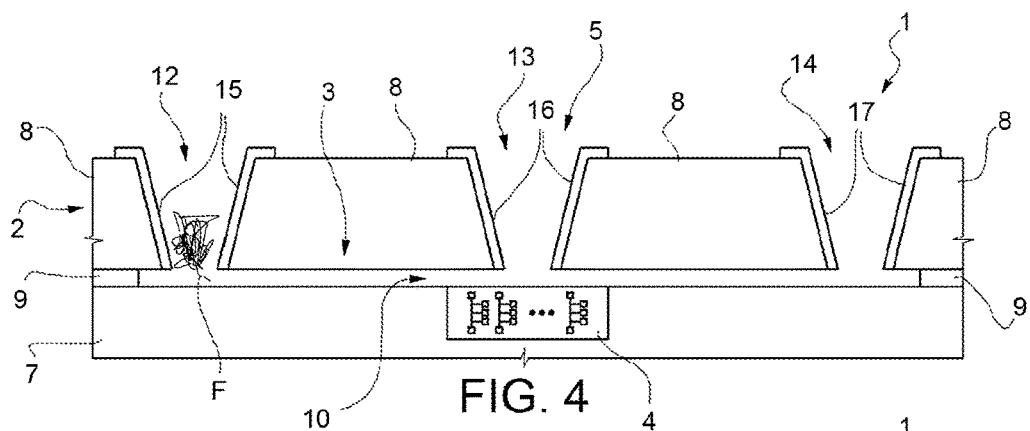
FIGS. 4-7 show the cross-sectional view of FIG. 1 in respective operating configurations.

With reference to FIGS. 1 and 2, an apparatus for nucleic acid sequencing is designated as a whole by the reference number 1 and comprises a body 2 housing a fluidic circuit 3, a base-detection device 4, and a conveying device 5, which is configured to control the movement of nucleic acid strands in the fluidic circuit 3.

In one embodiment, the body 2 comprises a first, supporting, structural layer 7 and a second structural layer 8, arranged between which is a spacer layer 9 of nanometric thickness (for example, less than 20 nm). The first structural layer 7 may, for example, be a substrate of intrinsic semiconductor material, or else may be of polymeric material or some other non-conductive material. Alternatively, the first structural layer 7 could also be of a doped semiconductor material and be electrically insulated from the fluidic circuit 3, for example by a dielectric layer delimiting the fluidic circuit 3 itself. The second structural layer 8 and the spacer layer 9 may be, for example, respectively, of aluminum nitride (or else of intrinsic silicon or some other non-conductive or conductive material insulated from the fluidic circuit 3) and of silicon oxide.

In use, the fluidic circuit 3 is filled with a solution containing denatured strands of a nucleic acid and comprises a nanochannel 10, which, in one embodiment, is defined between the first structural layer 7 and the second structural layer 8. Denaturing may be obtained also directly in the fluidic circuit 3, upstream of the inlet of the nanochannel 10. The nanochannel 10 extends longitudinally along an axis A for a length for example comprised between 100 µm and 500 µm and has a cross-section, perpendicular to the axis A, of nanometric dimensions, in particular, less than 100 nm (for example 20×20 nm). The transverse dimensions of the nanochannel 10, in a direction perpendicular to its length, are selected for favoring passage of a single extended strand of nucleic acid, as in the case of the nanopores described in the articles cited above. In particular, in the example described herein, the nanochannel 10 has a height and a width equal to the thickness of the spacer layer 9. In other embodiments not shown, however, the nanochannel 10 may have a different cross-section, for example rectangular, triangular, or circular.

The fluidic circuit 3 comprises an inlet well 12, a control well 13, and a collection well 14, all defined by respective openings through the second structural layer 8. In particular, the nanochannel 10 is accessible from outside through the inlet well 12 to enable introduction of the solution to be analyzed.

Techniques for providing nanometric fluidic structures, in particular, nanochannels, are known, for example from the published patent application No. US 2013/0213815 A1, which is incorporated herein by reference in its entirety.

In one embodiment, the conveying device 5 (see also FIG. 3) comprises: a first electrode 15, a second electrode 16, and a third electrode 17, which are arranged along the fluidic circuit 3 and are configured to apply respective voltages to a fluid present in the fluidic circuit 3; a first impedance-meter stage 18 and a second impedance-meter stage 19; and a control unit 20.

In one embodiment, the first electrode 15, the second electrode 16, and the third electrode 17 are arranged on a face of the second structural layer 8 opposite to the first structural layer 7 and coat the side walls, respectively, of the inlet well 12, of the control well 13, and of the collection well 14. In particular, the first electrode 15, the second electrode 16, and the third electrode 17 extend substantially as far as the nanochannel 10 for coming into contact with the solution loaded into the nanochannel 10 itself.

The base-detection device 4 is located in a detection site along the nanochannel 10 in the proximity of the second electrode 16, so as to interact with an extended strand of nucleic acid, advancing in the nanochannel 10 in the detection site. The base-detection device 4 is configured to recognize individual bases or sequences of a programmed number of bases (for example four) in a portion of the strand that is advancing in the detection site. The raw sequence of the bases recognized by the base-detection device 4 is supplied to the control unit 20, which, if necessary, orders the raw sequence in an effective base sequence SEQ (FIG. 3) as explained in detail hereinafter, in order to take into account the detection modality and possible geometrical constraints of the base-detection device 4.

The first impedance-meter stage 18 and the second impedance-meter stage 19 are connected for measuring, respectively, an electrical impedance Z' between the first electrode 15 and the second electrode 16 and an electrical impedance Z" between the second electrode 16 and the third electrode 17. The values of impedance Z', Z" measured are determined by the state of the nanochannel 10 and are supplied to the control unit 20. More precisely, the electrical impedance in a stretch of the nanochannel 10 containing the solution increases when a portion of a nucleic acid strand is present. The first impedance-meter stage 18 and the second impedance-meter stage 19 thus operate as presence sensors that detect the presence of a nucleic acid strand, respectively, in a first portion of the nanochannel 10, between the second electrode 16 and the first electrode 15, and in a second portion of the nanochannel 10, between the third electrode 17 and the second electrode 16. In other embodiments (not illustrated), presence sensors of a different type may be used.

The control unit 20 sets a first voltage $V_1$ on the first electrode 15, a second voltage $V_2$ on the second electrode 16, and a third voltage $V_3$ on the third electrode 17 as a function of the first impedance value Z' and of the second impedance value Z", respectively supplied by the first impedance-meter stage 18 and by the second impedance-meter stage 19.

As described in what follows, the voltages $V_1$, $V_2$, $V_3$ are each time selected on the basis of the impedance values Z', Z" so as to:

favor introduction of one end of a nucleic acid strand F into the nanochannel 10;

counter entry of further strands into the nanochannel 10 when this is already occupied;

control the speed and direction of advance of the strand F present in the nanochannel 10; and apply to a portion of the strand F present in the nanochannel 10 a force such as to cause stretching of the strand F itself, i.e., a condition in which consecutive bases are arranged at a greater distance apart from one another than in the case of absence of external forces.

Figure 5:
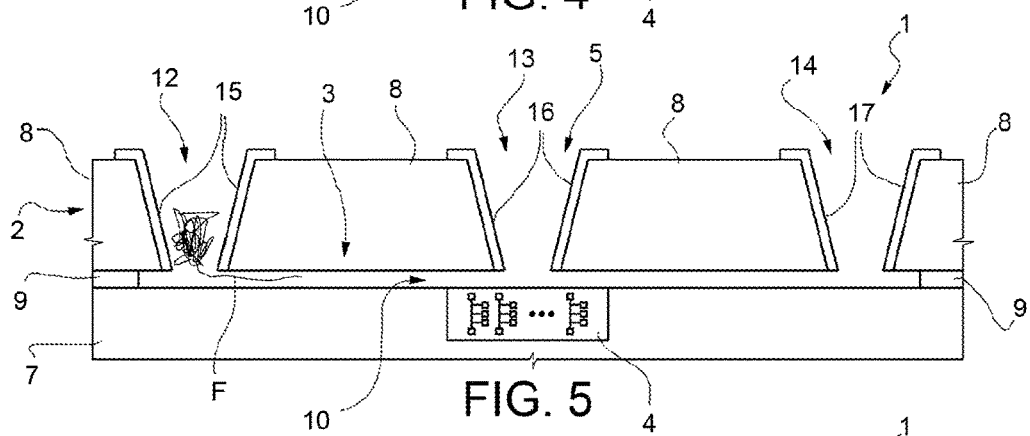
Figure 6:
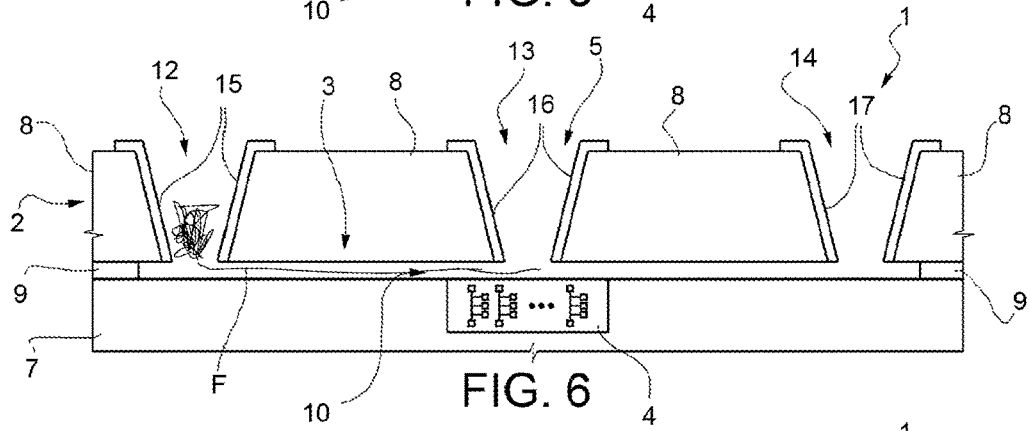
Figure 7:
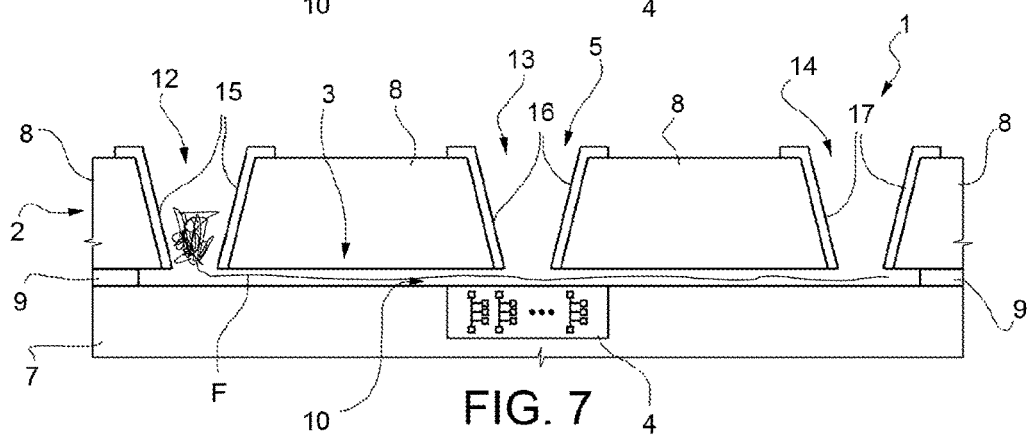

As is shown in FIG. 4, the inlet well 12 is initially filled with a solution containing denatured nucleic acid strands, which have a negative electrical charge. The nanochannel 10 is occupied exclusively by the solution and is free from strands. The first electrical impedance Z' has a respective first (low) value. The control unit 20 sets the first voltage $V_1$ to a negative value and the second voltage $V_2$ to a first positive value, so as to favor entry into the nanochannel 10 of one end of one of the nucleic acid strands present in the inlet well 12 (FIG. 5). The value of the third voltage $V_3$ in this step is indifferent and, for example, may be equal to the value of the second voltage $V_2$.

When the end of a nucleic acid strand F enters a first portion of the nanochannel 10, comprised between the inlet well 12 and the control well 13, where the base-detection device 4 is located, the first electrical impedance Z' detected by the first impedance-meter stage 18 starts to increase. In response to the increase of the first electrical impedance Z', the control unit 20 sets the first voltage $V_1$ to a positive value and increases the second voltage $V_2$ up to a respective second value, higher than the positive value of the first voltage $V_1$. The positive value of the first voltage $V_1$ enables attraction of further denatured strands within the inlet well 12, for example from a loading reservoir not illustrated. The second voltage $V_2$, higher than the first voltage $V_1$, produces an electrostatic force FE that attracts the end of the strand F present in the nanochannel 10 towards the second electrode 16 and the control well 13. The portion of the strand F still in the inlet well 12 unwraps as the end proceeds along the nanochannel 10.

When the end of the strand F present in the nanochannel 10 reaches the second electrode 16 and the control well 13, the control unit 20 sets the third voltage $V_3$ on the third electrode 17 to a value higher than the value of the second voltage $V_2$ on the second electrode 16 (which is thus intermediate between the first voltage $V_1$ and the third voltage $V_3$), for feeding the nucleic acid strand F along a second portion of the nanochannel 10, comprised between the control well 13, where the base-detection device 4 is located, and the collection well 14.

Entry of the strand F into the second portion of the nanochannel 10 causes an increase of the second electrical impedance Z", which is detected by the second impedance-meter stage 9. In response to the increase in the second electrical impedance Z", the control unit 20 sets the values of the voltages $V_1$, $V_2$, $V_3$ so as to favor removal of any possible obstruction from the first portion of the nanochannel 10. In fact, even though introduction of a further nucleic acid strand into the nanochannel 10 already occupied is highly unlikely on account of the dimensions, an event of this type cannot be ruled out. In one embodiment, the control unit 20 thus applies forces that tend to remove an additional strand from the nanochannel 10 already occupied. In particular, the control unit 20 sets the third voltage $V_3$ to a value higher than both the first voltage $V_1$ and the second voltage $V_2$, and the first voltage $V_1$ to a value higher than the second voltage $V_2$ and thus intermediate between the second voltage $V_2$ and the third voltage $V_3$. In this way, the strand F that has already reached the second portion of the nanochannel 10 is withheld, because the higher contribution of the third voltage $V_3$ prevails. Any possible strands further present in the first portion of the nanochannel 10 are instead expelled, because the electrostatic force FE determined by the first voltage $V_1$ and by the second voltage $V_2$ pushes the nucleic acids, which are negatively charged, towards the inlet well 12. The nanochannel 10 is thus freed from the presence of possible additional strands.

Once the procedure of removal of possible obstructions has been carried out, the control unit 20 sets once again the voltages $V_1$, $V_2$, $V_3$ so as to control advance and stretching of the strand F present in the nanochannel 10.

More precisely, the difference between the third voltage $V_3$ and the first voltage $V_1$ determines the speed and direction of advance of the nucleic acid strand F along the nanochannel 10. When the third voltage $V_3$ is higher than the first voltage $V_1$, the strand F proceeds from the inlet well 12 towards the collection well 14. When, instead, the third voltage $V_3$ is lower than the first voltage $V_1$, the nucleic acid strand F moves in the opposite direction, from the collection well 14 to the inlet well 12. The absolute value of the difference between the third voltage $V_3$ and the first voltage $V_1$ determines the speed of advance of the strand F.

The difference between the third voltage $V_3$ and the second voltage $V_2$, instead, determines stretching of the nucleic acid strand F that is advancing in the detection site. In the absence of applied external forces, consecutive bases of a nucleic acid strand are arranged apart from one another with an approximately constant pitch (around 0.33 nm). The electrostatic force FE due to the difference between the third voltage $V_3$ and the second voltage $V_2$ acts upon the extended strand F and causes a separation between consecutive bases, in particular, at the detection site. The distance between consecutive bases may thus be controlled and adapted for optimizing the performance and reliability of the base-detection device 4. Furthermore, if the base-detection device 4 is based upon hybridization of target oligonucleotides, it is possible to control the force on the strand F being examined for favoring hybridization and subsequently separate the strand F and the hybridized target oligonucleotide mechanically.

The conveying device 5 thus enables an extremely fine and flexible control of the movement of the nucleic acid strands along the nanochannel 10. The use of the three electrodes 15, 16, 17 in fact enables control not only of the direction and speed of advance, but also of the force exerted on the portion of the strand F being examined in the base-detection device 4.

Figure 8:
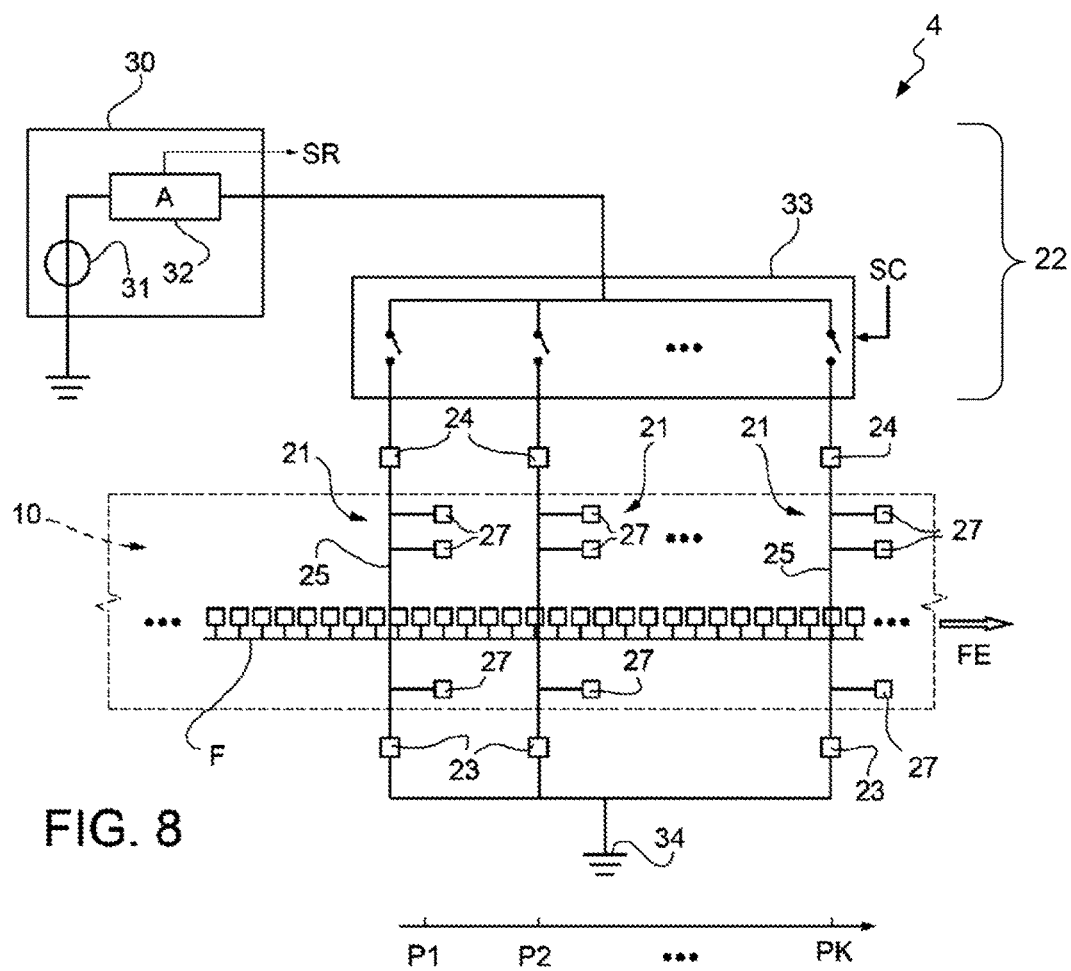
FIG. 8 is a more detailed block diagram of a portion of the apparatus of FIG. 1.

In one embodiment, the base-detection device 4 comprises a plurality of nanowire detectors 21 and a reading circuit 22, as is shown in FIG. 8. The nanowire detectors 21 are arranged in respective positions P1, P2, ... PK along the nanochannel 10 at the detection site. Each nanowire detector 21 provides a field-effect device and comprises a source region 23, a drain region 24, and a nanowire 25, which connects the source region 23 and the drain region 24. The source region 23 and the drain region 24 are of semiconductor material having a first type of conductivity, for example N+, and are opposite with respect to a region of passage of the nucleic acid strands that are advancing in the detection site, in particular, with respect to the axis A of the nanochannel 10. The semiconductor material may for example be silicon, germanium, InP, GaN. The nanowire 25 is of the same semiconductor material as that of the source region 23 and drain region 24, but has a second type of conductivity, for example P. The nanowire 25 defines a channel region between the source region 23 and the drain region 24. The conductance of the nanowire 25 is determined by the presence of electrical charge around the nanowire 25 itself. In particular, a negative charge in the vicinity of the nanowire 25 causes a drop of the conductivity with respect to a condition of neutral charge.

The nanowires 25 of the nanowire detectors 21 are arranged in a direction transverse with respect to the axis A of the nanochannel 10 in the detection site so that a nucleic acid strand advancing along the nanochannel 10 itself will traverse the nanowires 25. In one embodiment, the nanowires 25 are parallel to one another and are arranged in succession along the nanochannel 10.

Figure 9:
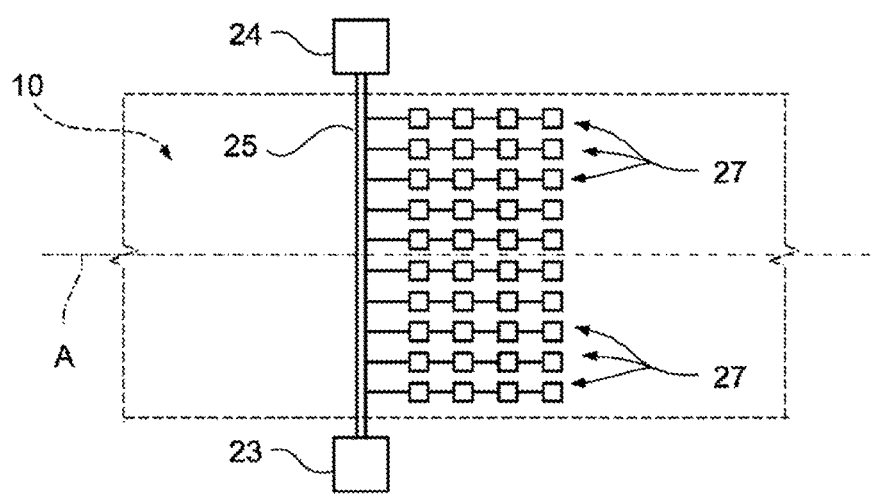
FIG. 9 shows an enlarged detail of the apparatus of FIG. 1.

Each nanowire 25 is functionalized with respective nucleic acid probes 27. The nucleic acid probes 27 are defined by oligonucleotides with the same number N of bases, for example four, as in the example of FIG. 9. In one embodiment, the nucleic acid probes 27 have the structure of a peptidonucleic acid (PNA), which contains repeated units of N-(2-aminoethyl)-glycine joined by peptide bonds and is electrically neutral. Associated to each nanowire 25 are nucleic acid probes 27 of the same type (i.e., containing the same base sequences). Given that the nucleic acid probes 27 are electrically neutral, their presence does not modify the state of conduction of the respective nanowire detector 21. However, the nucleic acid probes 27 may hybridize to corresponding base sequences in the nucleic acid strands advancing in the nanochannel 10. In this case, the sequence of the hybridized nucleic acid is withheld in the proximity of the corresponding nanowire 25 and with its own negative charge causes an increase of impedance of the nanowire detector 21.

In other embodiments (not illustrated), the nucleic acid probes may have a DNA or RNA structure. In these cases, the probes themselves are negatively charged. Hybridization with corresponding sequences of the strand F causes in any case a variation of charge and, consequently, a detectable variation of the impedance of the nanowires.

The nanowires 25 and the respective nucleic acid probes 27 exhaust the $4^N$ combinations that may be obtained with the number N of bases contained in each nucleic acid probe 27 (the bases available to form nucleic acids are in any case four: two purines—adenine and guanine—and two pyrimidines—cytosine and thymine for DNA, cytosine and uracil for RNA). In the example described, the possible combinations of four bases are $4^4=64$, and there are present as many nanowires 25, each with a nucleic acid probe 27 of a respective type. Furthermore, each nanowire 25 occupies a respective position P1, P2, ... , PK (where $K=4^N$ is the number of possible combinations of bases) along the nanochannel 10.

The reading circuit 22 is configured to determine the state of conduction of each of the nanowire detectors 21, for example by impedance detection. In one embodiment, the reading circuit 22 comprises an impedance-meter stage 30, for example including a voltage source 31 and a current sensor 32, and a multiplexer 33, configured to connect the impedance-meter stage 30 selectively to one of the nanowire detectors 21, in particular, to the drain region 24 (the source regions 23 of the nanowire detectors 21 are connected to a reference-potential line 34, for example a ground line).

As has been mentioned, when the nucleic acid probes 27 of one of the nanowire detectors 21 hybridize a corresponding sequence of the nucleic acid strand F advancing in the nanochannel 10, the negative charge of the strand F causes an increase of impedance of the nanowire 10, which is detected by the impedance-meter stage 30.

Figure 10:
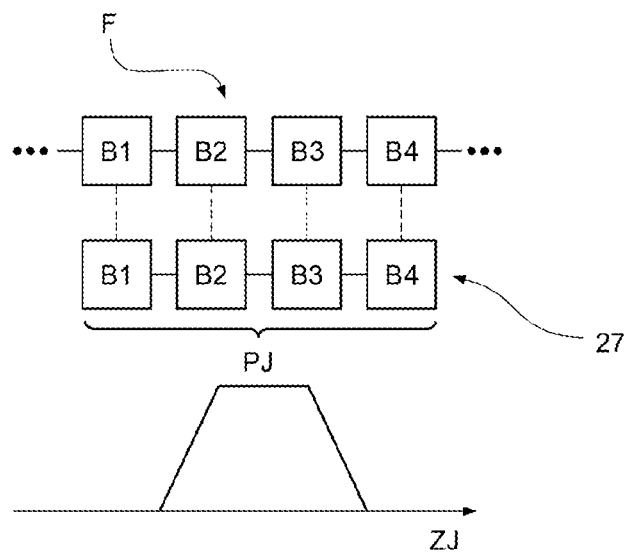
FIGS. 10-12 are graphs that show electrical quantities regarding the apparatus of FIG. 1.

The control unit 20 queries the base-detection device 4, which, in response to the queries, supplies information regarding the bases of the nucleic acid strand F advancing in the nanochannel 10. In detail, the control unit controls the multiplexer 33 by a control signal SC so as to connect the impedance-meter stage 30 in rotation to each of the nanowire detectors 21, and receives in response a read signal SR indicating the state of conduction of the nanowire detectors 21 connected to the impedance-meter stage 30 and, consequently, the presence of the respective set of bases in the portion of the nucleic acid strand F that is advancing in the detection site. More precisely, an increase of impedance of one of the nanowire detectors 21 (for example, in position PJ) indicates the presence of a respective sequence of bases (four, in the example described) in the portion of the nucleic acid strand F that is advancing in the detection site, as illustrated in FIG. 10. The succession of the read signals SR defines the raw sequence supplied by the base-detection device 4.

Figures 11, 12:
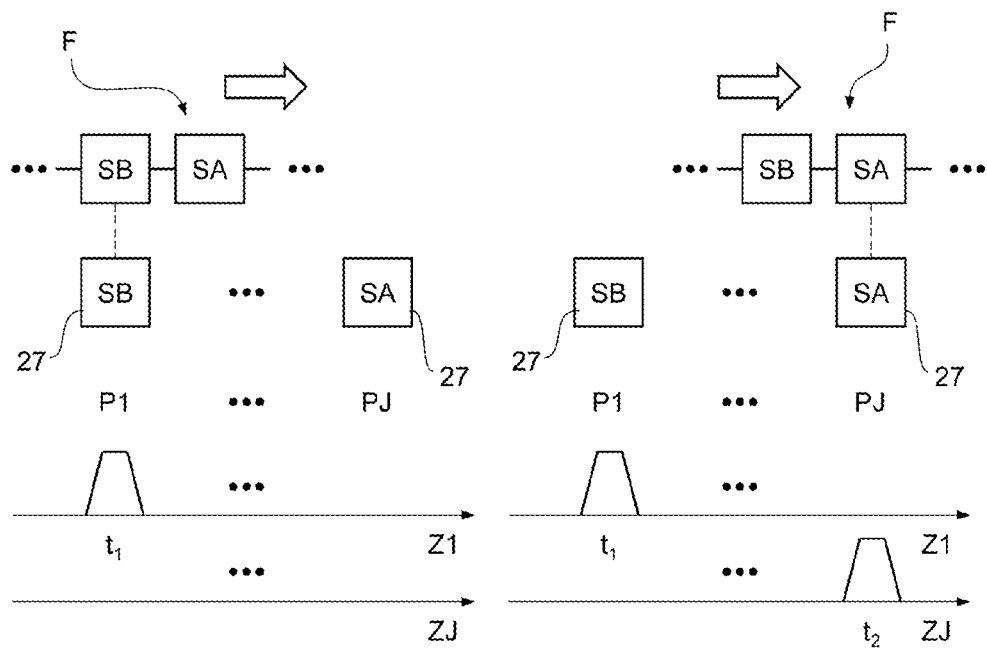

The control unit 20 reconstructs the effective base sequence SEQ that forms the nucleic acid strand F on the basis of the read signals SR received, taking into account the instants at which the read signals SR are generated and the positions P1, P2, . . . , PK occupied by the respective nanowires 25 along the nanochannel 10. In one embodiment, each sequence of bases recognized by the base-detection device 4 is translated, in the effective base sequence SEQ, by a number of positions such as to compensate the detection delay due to the distance between the generic position PJ of the hybridized nanowire detector 21, which has positively made a detection, and the position P1 of the first nanowire detector 21 reached by the nucleic acid strand F. For instance, if the nucleic acid strand F that is advancing in the detection site contains a sequence SA of N bases that may be detected by the nanowire detector 21 in position PJ, followed by a sequence SB of N bases that may be detected by the nanowire detector 21 in position P1, the base-detection device 4 recognizes the sequence SB before the sequence SA (FIGS. 11 and 12: the impedance Z1 of the nanowire detector 21 corresponding to the sequence SAn increases before the impedance ZJ of the nanowire detector 21 corresponding to the sequence SB). The control unit 20 re-aligns the sequences SA and SB and compensates the delay with a relative shift of J−1 positions of the sequence SB with respect to the sequence SA. Re-alignment may be obtained either by translating the sequence SB J−1 positions forwards or by translating the sequence SA J−1 positions backwards. More in general, re-alignment between a sequence detectable by the nanowire detector 21 in position PI and a sequence detectable by the nanowire detector 21 in position PJ (J>I) is obtained with a relative shift of J−I−1 positions in the effective base sequence SEQ. Translation in the effective base sequence SEQ of the raw sequence of the read signals SR may be obtained, for example, by entering the base sequences corresponding to the read signals SR into a shift register in positions translated with respect to a reference position as a function of the position of the nanowire detector 21.

The control unit 20 may also take into account possible overlaps in the sequences recognized by the base-detection device 4. For instance, a sequence containing the bases AAAAC may be recognized both by the nanowire detector 21 associated to which are nucleic acid probes 27 with the sequence AAAA and by the nanowire detector 21 associated to which are nucleic acid probes 27 with the sequence AAAC. The overlapping portion (in this case AAA) may be used as check on the correctness of recognition.

The apparatus 1 according to the disclosure, thanks, in particular, to the base-detection device 4, enables a complete scan to be carried out of the entire nucleic acid strand, without having to resort to techniques of fragmentation, identification of the subsequences, and recomposition. On the one hand there is thus eliminated the possibility of portions of the sequence being lost due to errors in the recomposition of the subsequences. The scan is actually complete. On the other hand, the resources for processing downstream of the base-recognition process are very reduced, given that to reconstruct the effective sequence a translation of the bases as a function of the position of the nanowire detectors that carry out recognition is sufficient.

Finally, it is evident that modifications and variations may be made to the device and to the method described, without thereby departing from the scope of the present disclosure.

In particular, it is possible to use conveying devices that differ from the one described. For instance, the conveying device may be based upon a wall with a nanopore through which the nucleic acid strand is made to pass and extend as a result of electrostatic forces. These are obtained by sets of electrodes located on opposite sides with respect to the wall. The electrodes are driven for favoring entry of one end of the strand into the nanopore and subsequently getting the entire strand slide through the nanopore itself, unwrapping it. The base-detection device is arranged on the outlet side of the nanopore, where the strand proceeds in an extended condition.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An apparatus for nucleic acid sequencing, comprising:
    a base-detection device in a detection site, the base-detection device being configured to detect bases of a portion of a nucleic acid strand at the detection site;
    a conveying device configured to extend the nucleic acid strand and to cause the nucleic acid strand to slide through the detection site along a path; and
    a structural layer having a first portion enclosing a first portion of the path, a second portion enclosing a second portion of the path, and an opening between the first portion and the second portion of the structural layer, the opening being aligned with the detection site;
    wherein the base-detection device comprises a plurality of nanowire detectors arranged along the path, each nanowire detector of the plurality of nanowire detectors including a respective nanowire and one or more nucleic acid probes, which are fixed to the respective nanowire, each nucleic acid probe of the one or more nucleic acid probes fixed to the respective nanowire having the same sequence of nucleic acid bases.

2. The apparatus according to claim 1, wherein the one or more nucleic acid probes of the plurality of nanowire detectors each contain an equal number of bases.

3. The apparatus according to claim 2, wherein the one or more nucleic acid probes of the plurality of nanowire detectors exhaust the possible combinations of bases that may be obtained with the number of bases forming the nucleic acid probes.

4. The apparatus according to claim 1, wherein the one or more nucleic acid probes have a peptidonucleic acid structure.

5. The apparatus according to claim 1, wherein the respective nanowires of the plurality of nanowire detectors are arranged in a direction transverse to the path and parallel to one another.

6. The apparatus according to claim 1, wherein each nanowire detector of the plurality of nanowire detectors comprises a source region and a drain region at opposite sides with respect to the path and are connected together by the respective nanowire of the nanowire detector.

7. The apparatus according to claim 6, wherein, in each nanowire detector of the plurality of nanowire detectors, the source region, the drain region and the respective nanowire are of semiconductor material and wherein the source region and the drain region have a first type of conductivity, and the respective nanowire has a second type of conductivity, opposite to the first type of conductivity.

8. The apparatus according to claim 1, wherein the base-detection device comprises a reading circuit configured to determine a state of conduction of each nanowire detector of the plurality of nanowire detectors.

9. The apparatus according to claim 8, wherein the reading circuit is configured to provide a succession of read signals indicating base sequences present in the nucleic acid strand and corresponding to respective nucleic acid probes of the plurality of nanowire detectors.

10. The apparatus according to claim 9, wherein the reading circuit comprises an impedance-meter stage and a multiplexer configured to connect the impedance-meter stage selectively to a nanowire detector of the plurality of nanowire detectors.

11. The apparatus according to claim 9, further comprising a control unit configured to reconstruct an effective base sequence of the nucleic acid strand based on the read signals supplied by the reading circuit and positions of one or more nanowire detectors of the plurality of nanowire detectors on the path.

12. The apparatus according to claim 1, wherein the conveying device is configured to control advance of the nucleic acid strand along the path by an electrostatic force that enables hybridization of the nucleic acid strand and a nucleic acid probe of the one or more nucleic acid probes, and separation of the nucleic acid strand from the nucleic acid probe of the one or more nucleic acid probes.

13. The apparatus according to claim 1, wherein:
the path is a nanochannel;
the conveying device comprises a first electrode, a second electrode, and a third electrode arranged along the nanochannel to be in contact with a fluid occupying the nanochannel, the second electrode being arranged between the first electrode and the third electrode; and
the apparatus further comprises a control unit configured to apply a first voltage, a second voltage, and a third voltage to the first electrode, the second electrode, and the third electrode, respectively, so as to control movement of the nucleic acid strand through the nanochannel.

14. The apparatus according to claim 13, wherein the path is defined by a longitudinal axis of the nanochannel.

15. The apparatus according to claim 13, wherein the base-detection device is arranged in the proximity of the second electrode.

16. The apparatus according to claim 13, comprising a first presence sensor and a second presence sensor, which are configured to detect the presence of the nucleic acid strand, the first presence sensor being in a first portion of the nanochannel, between the first electrode and the second electrode, and the second presence sensor being in a second portion of the nanochannel, between the second electrode and the third electrode; and wherein the control unit is configured to set the first voltage, the second voltage, and the third voltage on the basis of a response of the first presence sensor and of the second presence sensor.

17. A method for nucleic acid sequencing, comprising:
extending a nucleic acid strand;
causing the nucleic acid strand to slide along a path that is partially enclosed by a structural layer having a first portion enclosing a first portion of the path, a second portion enclosing a second portion of the path, and an opening between the first portion and the second portion of the structural layer, the opening being aligned with a detection site comprising nanowire detectors arranged in respective positions along the path, each nanowire detector having a nanowire, arranged in a direction transverse to the path, and one or more nucleic acid probes fixed to the nanowire, each nucleic acid probe fixed to a particular nanowire having the same sequence of nucleic acid bases;
iteratively identifying nucleic acid probes hybridized by the nucleic acid strand;
determining a raw sequence of bases based on the nucleic acid probes hybridized by the nucleic acid strand; and
reconstructing an effective base sequence that forms the nucleic acid strand based on the raw sequence, the respective positions of the nanowire detectors corresponding to the nucleic acid probes hybridized by the nucleic acid strand, and a detection delay due to a distance between a position of a first nanowire detector of the nanowire detectors reached by the nucleic acid strand and a position of a particular nanowire detector of the nanowire detectors.

18. The method according to claim 17, wherein causing the nucleic acid strand to slide comprises applying an electrostatic force to the nucleic acid strand so as to enable hybridization of the nucleic acid probes and separation of the nucleic acid strand from the nucleic acid probes.

19. An apparatus for nucleic acid sequencing, comprising:
a channel comprising a path and a structural layer enclosing a first portion of the path and a second portion of the path, the structural layer having an opening between the first portion and the second portion of the path, the opening being aligned with a detection site;
a base-detection device in the detection site, the base-detection device being configured to detect bases of a portion of a nucleic acid strand at the detection site; and
a conveying device configured to extend the nucleic acid strand and to cause the nucleic acid strand to slide through the detection site along the path, wherein the base-detection device comprises:
- a plurality of nanowire detectors arranged in respective positions along the path, each nanowire detector including a respective nanowire and one or more nucleic acid probes, which are fixed to the respective nanowire, each nucleic acid probe fixed to the respective nanowire having the same sequence of nucleic acid bases;
- a reading circuit configured to provide a succession of read signals indicating base sequences present in the nucleic acid strand and corresponding to respective nucleic acid probes of the nanowire detectors; and
- a control unit configured to reconstruct an effective base sequence of the nucleic acid strand based on the read signals supplied by the reading circuit, the respective positions of the nanowire detectors along the path, and a detection delay due to a distance between a position of a first nanowire detector of the plurality of nanowire detectors reached by the nucleic acid strand and a position of a particular nanowire detector of the plurality of nanowire detectors.

20. The apparatus according to claim 19, wherein each nanowire detector comprises a source region and a drain region at opposite sides with respect to the path and are connected together by the respective nanowire of the nanowire detector.

21. The apparatus according to claim 20, wherein, in each nanowire detector, the source region, the drain region and the respective nanowire are of semiconductor material and wherein the source region and the drain region have a first type of conductivity, and the respective nanowire has a second type of conductivity, opposite to the first type of conductivity.

22. The apparatus according to claim 19, wherein the conveying device is configured to control advance of the nucleic acid strand along the path by an electrostatic force that enables hybridization of the nucleic acid strand and a nucleic acid probe of the one or more nucleic acid probes, and separation of the nucleic acid strand from the nucleic acid probe of the one or more nucleic acid probes.

* * * * *